United States Patent [19]
Wilkinson et al.

[11] Patent Number: 5,871,804
[45] Date of Patent: Feb. 16, 1999

[54] FLOURESCENT LIPID REAGENT

[75] Inventors: Della A. Wilkinson; John E. Watkin, both of Ottawa, Canada

[73] Assignee: Her Majesty the Queen in right of Canada as represented by the Solicitor General Acting Through the Commissioner of the Royal Canadian Mounted Police, Ottawa, Canada

[21] Appl. No.: 494,074

[22] Filed: Jun. 23, 1995

[51] Int. Cl.$^6$ ........................................... A61B 5/117
[52] U.S. Cl. .................. 427/1; 427/145; 427/384
[58] Field of Search .................. 427/1, 145, 384

[56] References Cited

U.S. PATENT DOCUMENTS 5,342,645  8/1994  Eisele et al. .................. 427/1
5,348,159  9/1994  Watkin .......................... 427/1

*Primary Examiner*—Janyce Bell
*Attorney, Agent, or Firm*—J. Wayne Anderson

[57] ABSTRACT

The invention disclosed relates to a composition and method for enhancing the contrast of the lipid component of fingerprints and the like. The composition includes a metal chelate of the structural formula I

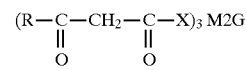

wherein R is a UV-absorbing aromatic group, X is an electron attracting group, G is a synergic group containing a suitable polar functional group, and M is a metal ion, a suitable water-soluble organic solvent and water, at pH of 3 to 10.

11 Claims, 2 Drawing Sheets

FLOURESCENT LIPID REAGENT

BACKGROUND OF THE INVENTION

1. Field of the Invention

This invention relates to the detection of fingerprints and the like, and in particular to the enhancement of lipid fingerprints on porous and other surfaces.

Sweat glands are located all over the body except for the soles of the feet whereas sebaceous glands are found primarily on the face, neck, upper chest and upper back. Although only secreted over a relatively small area of the skin the sebum (lipids), which are viscous liquids at the skin surface temperature of 32° C., will diffuse over the entire area. Fingerprints are comprised of sweat and sebum in varying quantities. Although sebum is not directly secreted onto the fingers it is easily transferred in significant amounts by frequent contact of the hands and fingers with the face. The exact composition of the fingerprint not only varies from one individual to the next but will also vary for each individual depending upon many uncontrolled factors such as the time of day, the time period since washing the hands, the temperature, whether the individual frequently touches their face with their hands as well as any circumstances that may lead to excessive sweating such as stress or physical exercise.

Fingerprints that have been deposited onto surfaces that are then subjected to water will only be comprised of lipids since the water removes the water soluble components such as amino acids and leaves the water insoluble components such as lipids. In these circumstances the fingerprint can only be visualised using a lipid detection method.

Fingerprints that have been deposited onto cocaine exhibits are extremely difficult to visualize since the drug reacts with cyanoacrylate which is the chemical treatment most commonly used for the plastic packaging in which cocaine is usually contained. The use of chemicals for the visualisation of amino acids is restricted to porous surfaces excluding plastics. The fingerprint may be visualised using a lipid detection technique which does not interact with the cocaine.

2. Description of the Prior Art

A number of techniques for the detection of fingerprints have been documented.

Fingerprints developed by 1,8-diazofluoren-9-one (DFO) and Ninhydrin (followed by zinc chloride toning) on porous surfaces such as paper and cardboard are well recorded in the literature. For example, see The Use of 1,8-diazafluoren-9-one (DFO) for the Fluorescent Detection of Latent Fingerprints on Paper, a Preliminary Evaluation, Pounds et al., Journal of Forensic Sciences, JFSCA, vol. 35, No. 1, January, 1990. More specifically, these treatments react with the amino acid content of the fingerprint resulting in fluorescent images of the ridges which tend to be spotty in appearance. The ridges of the fingerprint are lined with sweat pores and the amino acids are contained within the sweat component of the fingerprint which explains the spotty pattern of fingerprints visualised by these methods.

One drawback with these fluorescent dyes is the requirement for an expensive light source in the price range of $10–20,000 for forensic lamps. Such costly equipment restricts the availability of this technology to police forces which have large budgets.

Another drawback is the spotty nature of the images obtained with amino acid detection techniques. The interpretation of the ridge detail and the comparison to a known sample is made that much harder when the ridges of the fingerprint do not appear as a continuous image. A ridge ending may well be confused with an unusually large gap between two consecutive sweat pores. In addition these techniques do not work for porous material that has been exposed to water since the amino acids are water soluble and will be removed from the fingerprint residue.

Fingerprints developed by physical developer on porous surfaces that have been exposed to water are also well documented in the literature. More specifically, the fingerprints develop a dark grey silver residue on their ridges which is visible to the naked eye providing the background is not heavily patterned or dark.

The main drawback with physical developer is that the technique is not fluorescent and therefore the ability to remove any complicated background patterns by using filters that only allow the wavelength corresponding to the fluorescence through can not be applied. In addition physical developer is a very expensive technique approximately $275 (canadian) for 4 litres and it has a shelf-life of about one year.

The application of europium for visualising fingerprints on paper has been described in the literature by E. R. Menzel (Fluorescent Metal-Ruhemann's Purple Coordination Compounds: Applications to Latent Fingerprint Detection, Journal of Forensic Sciences, JFSCA, Vol. 35, No. 1, January, 1990, pp. 25–34). Latents were reacted with ninhydrin which yields the product Ruhemann's Purple. This compound was then reacted with europium ions as opposed to zinc ions to form a weakly fluorescent chelate when viewed under laser light. This method is very inefficient and expensive, as time-resolved imaging is required to minimize the background fluorescence.

SUMMARY OF THE INVENTION

According to one aspect of the invention, a composition for enhancing the contrast of the lipid component of fingerprints and the like is provided, comprising of the metal chelate of the structural formula I,

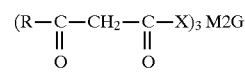

$$(R-\underset{\underset{O}{\|}}{C}-CH_2-\underset{\underset{O}{\|}}{C}-X)_3 M2G \qquad I$$

wherein R is an aromatic group capable of absorbing UV light,

X is an electron attracting group,

G is a synergic group containing a polar functional group, and

M is a suitable metal ion which upon exposure to sufficient UV radiation, intramolecularly receives UV energy absorbed by the chelate and emits the energy as visible fluorescence in a narrow wavelength emission band characteristic of the metal, a suitable water-soluble organic solvent, and water; at pH of 3 to 10.

It is believed that the synergic group coordinates to the metal M, creating (together with the ligand) a non-polar shell around the metal ion which increases the quantum yield. This results in brighter fingerprint fluorescence than if no synergic group were present.

The metal chelate of structural formula I is dissolved in an aqueous solution of an organic solvent which possesses the following properties;

(a) miscible in water to some extent; and, (b) soluble in lipids to some extent.

In addition the aqueous solution may contain a suitable surfactant which improves the solubility properties of the water insoluble metal chelate. Sodium tetradecyl sulfate, sold under the trademark Tergitol 7, has been found most effective.

Treating the lipid fingerprint with this solution results in the transfer of the chelate into and onto the lipids of the fingerprint. On removal of the fingerprint from the solution the solvents evaporate leaving the metal chelate in and on the fingerprint. Excessive metal chelate deposited on the background may be removed by immersion in a solution containing a compound that will destroy the fluorescent chelate and form a non-fluorescent chelate with the metal ion. The compound is a chemical that is capable of replacing the UV absorbing organic ligand as well as being capable of acting as an organic ligand by coordinating to the metal ions. The resulting metal chelate is non-fluorescent and will not be visible under UV light. Suitable compounds include citric acid and the sodium salt of (ethylenediaminetetraacetic acid) EDTA, the latter being preferred. Illumination by UV light will not visualize the non-fluorescent chelate only the fluorescent chelate contained within the lipids of the fingerprint.

According to another aspect of the invention, a method for visualising the lipid component of fingerprints and the like is provided, comprising (a) treating fingerprints with a composition comprising of a metal chelate of structural formula I,

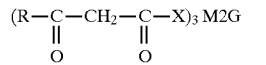

wherein R is an aromatic group capable of absorbing UV light,

X is an electron attracting group,

G is a synergic group containing a polar functional group, and M is a suitable metal ion which upon exposure to sufficient UV radiation, intramolecularly receives UV energy absorbed by the chelate and emits the energy as visible fluorescence in a narrow wavelength emission band characteristic of the metal, a suitable water-soluble organic solvent, and water; and wherein the pH of said composition is 3 to 10, to form a two-phase solution of (i) the solvent and water including dissolved chelate, and (ii) the solvent, excluding water but including dissolved chelate, in the lipid component, wherein the dissolved chelate is transferred into the lipid component through the organic solvent, (b) evaporating the solvent, leaving the chelate trapped in the lipid component, and (c) illuminating with a suitable UV light source to excite the chelate.

DETAILED DESCRIPTION OF THE PREFERRED EMBODIMENTS

Figure 1:
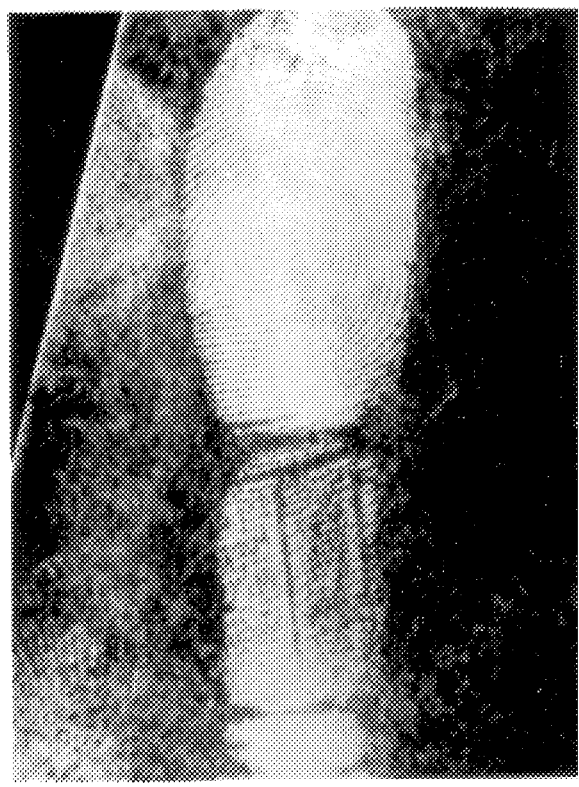
FIG. 1 is a drawing of a lipid fingerprint on xerox paper visualised by a composition according to the invention.

In the metal chelates of structural formula I,

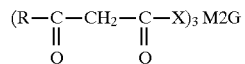

the R group is an aromatic UV-absorbing group including phenyl, substituted phenyl e.g. halo-substituted phenyl (such as fluorobenzene), heterocyclic aromatics (such as thiophene) and polycyclic aromatics (such as naphthyl). It will be appreciated that variations in the ring substituent will only shift the excitation wavelengths of the ligand, and provided that this wavelength remains in the UV region, the chelate will fluoresce in the red. Thiophene is preferred.

X is an electron attracting group. Specifically, an electron attracting group or atom is electronegative relative to its neighbouring atoms, and will withdraw electrons away from the neighbouring groups. Suitable groups include $CY_3$ group, wherein Y is halogen including F, Cl, Br, I and At, and a halo-benzene group such as fluorobenzene. $CF_3$ is preferred.

G is a polar synergic group that is capable of displacing water in order to co-ordinate to the metal M. Preferably, G displaces water from europium tris (theonyltrifluoroactone) dihydrate. Suitable groups include $R'_3PO$ wherein R' is an alkyl group which may be saturated or unsaturated, including aromatic groups such as phenyl; or substituted alkyl in which the substituents are other than polar groups which affect the coordination with the metal (M). Butyl and octyl are preferred, octyl being most preferred.

M is a suitable metal ion, preferably a lanthanide such as Tb and Eu which provides a narrow emission band (half-height of about 10 nm). In the case of Eu (III) which is most preferred, this band is centred at about 614 nm, thus giving an exceptionally large Stokes shift of about 260 nm.

For example, the chelate in which R is thiophene, X is $CF_3$, G is $(C_8H_{18})_3PO$, and M is europium III (i.e. the tris chelate of thenoyltrifluoroacetone and the europium III ion with two trioctylphosphine oxide groups coordinating groups) may be synthesized as part of the enhancement process.

Specifically, the formation of a metal e.g. europium chelate involves an organic compound of the structural formula II

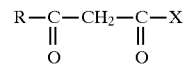

wherein R and X are defined as above and the addition of a compound containing the organic synergic group G, preferably G is $R'_3PO$, wherein R' is defined as above.

The chelate forms in an aqueous solution of pH 3 to 10, preferably containing a surfactant, typically Tergitol 7, as well as $Eu^{3+}$ ions, typically from a suitable europium salt e.g. $EuCl_3.6H_2O$, which forms a single phase with the water-soluble organic solvent, containing the chelating ligand and the synergic group. Other surfactants may be used, such as n-dodecylamine acetate in combination with synperonic N, a trademark for nonylphenol ethoxylate. Other europium salts may be used, such as the nitrate hydrate. If a buffer is desired tris-amine buffer is preferred because it has no carbonyl groups which could preferably react with the metal ion. The natural pH of the solution without buffer is pH 4 which reduces the fluorescence of the chelate in the solution but appears to not effect the fluorescence of the chelate within the lipid component of the fingerprint which is a non-aqueous environment.

Suitable organic solvents have the following properties:
water-soluble,
solubilizes metal chelate,
penetrates, but does not dissolve the lipid component of the fingerprint, while retaining the metal chelate in the lipid, and
volatile (to evaporate readily, following penetration of the lipid).

Suitable solvents include low molecular weight polar organic solvents incorporating a polar functional group, selected from a carbonyl group, and a hydroxyl group, such as alcohols and ketones. Specific suitable solvents include lower-alkyl alcohols (such as methanol, ethanol and 2-propanol) and acetone in water.

Lower alkyl alcohols are preferred. Methanol is most preferred.

This composition is suitable for visualising lipid fingerprints on many varied porous surfaces including paper and cardboard as well as non-porous surfaces such as plastics, metals and glass as will be apparent hereinafter.

The two bulky synergic groups make the chelate extremely insoluble in water and only slightly soluble in the organic solvent. When the fingerprints are treated with the composition according to the invention, the organic solvent penetrates the lipid component of the fingerprint without dissolving it and the chelate is transferred into the lipid component. Thus, a two phase system is established i.e. (i) solvent in water including dissolved chelate and (ii) solvent excluding water, but including dissolved chelate in the lipid component. Thus, the water insoluble metal chelate transfers into the solvent present within the lipid with a high partition ratio. The solvent is then removed by evaporation in air at room temperature. In other words, after removal from solution and evaporation of the solvent, the chelate remains trapped in the lipid component in greatly increased concentration over that in solution.

The metal chelate is also deposited on the surface of the lipid component since it is repelled by the aqueous system and attracted to the hydrophobic nature of the lipid component. The chelate retained within the lipid cannot be removed other than by dissolving the lipid component in a suitable organic solvent such as a higher ketone or alcohol.

Preferably, to further enhance the contrast, background fluorescence is minimized prior to UV illumination, by washing with a suitable non-fluorescent water-soluble chelating agent such as disodium EDTA ($Na_2EDTA$) or citric acid, to destroy the extraneous chelate and reacting with the liberated metal ion to form a non-fluorescent chelate. Most preferably, the wash solution comprises $Na_2EDTA$.

By these methods increased amounts of chelate are transferred into the lipid component of the fingerprint so that excitation by a cheap relatively low powered UV light source gives sufficient fluorescence to be easily seen by the eye.

The fluorescent fingerprint may then be viewed through goggles that block the ultraviolet light. For example, when using europium chelate, any background fluorescence from the substrate that is also excited by UV light may be greatly reduced by use of a narrow band (10 nm) interference filter centred at 620 nm and tilted slightly to pass a 614 nm central band.

Experimental

Formulation of europium chelate (1 litre) working solution 1) 23 mg of europium (III) chloride hexahydrate is dissolved in 300 ml of distilled water.

2) 2 ml of Tergitol 7 is added to the solution.

3) 45 mg of thenoyltrifluoroacetone is dissolved into 700 ml of methanol.

4) 50 mg of trioctylphosphine oxide is dissolved in the thenoyl solution.

5) The aqueous europium-containing solution is added to the methanol solution and mixed vigorously for 30 minutes with a magnetic stirrer.

It will be appreciated that the thenoyltrifluoroacetone and the trioctylphoshine oxide are provided in slight excess of the stoichiometric amount required to form the chelate.

Detection of fingerprints on porous surfaces

Most common porous surfaces where fingerprints are found in criminal investigations are writing paper, envelopes, cheques and envelopes. Before illumination by UV light, the porous materials are immersed for up to ten seconds in the working solution (70% methanol concentration) contained in a plastic tray with a resealable lid to reduce evaporation of the methanol. On other surfaces such as metals and plastics immersion for longer periods may be necessary.

On all surfaces after allowing for evaporation of the methanol the surfaces may be washed in a solution containing $Na_2EDTA$ ($8\times10^{-4}M$) or other water soluble chelating agents which form non-fluorescent chelates with europium III ions, to reduce and often completely remove the background fluorescence which is caused by extraneous dye adhering to the background surface.

Figure 2:
FIG. 2 is a drawing of lipid fingerprints on plastic bags visualised by a composition according to the invention.

FIGS. 1–2 show fluorescent prints on various surfaces photographed under UV light. A suitable light source is a 150 W mercury arc lamp that is completely blocked in the visible allowing only the 365 nm Hg line to pass the filter. Such lamps which produce an intensity of 7 $mW/cm^2$ at 15" distance are available from several commercial sources at a cost of a few hundred dollars.

Similar working solutions were made up as follows in the same manner, using the same materials and amounts as described above, except that in step 2 the surfactant was varied, in step 3, in the organic compound the R and X groups are varied and in step 4, in the synergic group the R' group is varied.

Specifically, a second working solution was made up wherein the surfactant was n-dodecylamine (0.2 g) and synperonic N (0.2 g).

The same procedure as described above was then followed for the detection of fingerprints on porous and non-porous surfaces.

The second working solution was observed to exhibit a bright intense fluorescence. Print transfer was excellent. Accordingly, the tergitol 7 is preferred.

Specifically, a third working solution was prepared wherein R is phenyl and X is $CF_3$.

In a fourth working solution R is naphthyl and X is $CF^3$.

In a fifth working solution, both R and X are fluorophenyl.

The same procedure as described above was then followed for the detection of fingerprints on porous and non-porous surfaces, using each of the similar working solutions, in turn.

The third working solution produces a clear solution which appeared brightly fluorescent. Print transfer was reasonable and the fingerprints were clearly visible.

The fourth and fifth working solutions produced cloudy solutions which appeared bright red under UV. Print transfer was reasonable and the fingerprints were clearly visible.

Accordingly, the thenoyltrifluoroacetone is preferred.

Specifically a sixth working solution was made up wherein the R' group of the synergic group was butyl.

The same procedure as described above for the detection of fingerprints on porous and non-porous surfaces was then followed.

The sixth working solution was observed to exhibit bright intense fluorescence. Print transfer was excellent.

Accordingly, the trioctylphosphine oxide is preferred.

We studied the effects of varying the organic solvent in step 3, using the thenoyltrifluoroacetone and trioctylphosphine oxide. Again the europium salt is dissolved in water, with no surfactant included. Specifically, the following solvents were employed 68% 2-propanol, 85% 1-butanol, 75% ethanol and 75% acetone.

For all solvents very intense solution fluorescence occurred. Transfer of dye into prints was reasonable but the background was brightly fluorescent for the alcohols. However, the fingerprints were still clearly visible.

For the 75% acetone solution, very intense solution fluorescence occurred. However, transfer of the dye into was reasonable butReasonable print transfer was observed but the background was very intensely fluorescent. Accordingly, methanol is preferred.

For field use, the lipid fingerprint enhancing composition according to the invention may be provided in the form of a kit.

Specifically, the kit comprises a combination of two components which are maintained apart until use by kit means. The kit means includes separate containers for the two components and associated packaging.

More specifically, a first component comprises an organic compound of structural formula II

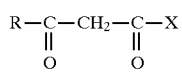     II wherein R and X are as defined above, as well as the synergic group of structural formula R'$_3$PO wherein R' is defined as above, and the second component comprises a suitable salt of a metal ion, such as europium III chloride hexahydrate which after reaction with the first component to form a chelate, intramolecularly receives energy absorbed by the chelate and emits the energy as visible fluorescence in a narrow wavelength emission band characteristic of the metal, dissolved in an aqueous solution preferably including a suitable surfactant e.g. Tergitol 7. The first component may be dissolved in a suitable organic solvent as described above, such as methanol.

For example, for a one litre working solution, a first reactant includes a concentrate of 45 mg of thenoyltrifluoroacetone and 50 mg of triocylphosphine oxide dissolved in 70 ml of methanol. The second reactant includes a concentrate of 23 mg of europium III chloride hexahydrate dissolved in 30 ml of an aqueous solution with 2 ml of tergitol 7 dissolved in the aqueous solution. At the time of use, a working solution would be completed by the addition of sufficient additional amounts of water and methanol. Vigorous mixing provides a working solution with a concentration of about 70% methanol in 1 litre of solution. Such a solution would be useful for use with porous and non-porous objects. It would be appreciated that various kits may be sold in which the amounts of the reactants in the two components are scaled up to provide different amounts of working solution.

We claim:

1. A method of enhancing the contrast of the lipid component fingerprints, comprising
   (a) treating fingerprints with a composition comprising metal chelate of structural formula I,

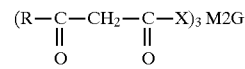     I wherein R is an aromatic group capable of absorbing UV light, X is an electron attracting group, G is a group containing a polar functional group and is capable of displacing water to co-ordinate to M, and M is a metal ion which upon exposure to sufficient UV radiation, intramolecularly receives UV energy absorbed by the chelate and emits the energy as visible fluorescence in a wavelength emission band characteristic of the metal, a water soluble organic solvent, a surfactant and water; wherein the pH of the composition is 3 to 10, to form a two phase solution of (i) the solvent and water including dissolved chelate and (ii) the solvent excluding water but including dissolved chelate, in the lipid component of the fingerprint,
   (b) evaporating the solvent leaving the chelate trapped in the lipid component of the fingerprint, and
   (c) illuminating with a suitable UV light source to excite the chelate.

2. A method according to claim 1, wherein the organic solvent includes a polar functional group selected from a carbonyl and a hydroxyl group.

3. A method according to claim 2, wherein the organic solvent is a lower-alkyl alcohol.

4. A method according to claim 3, wherein the organic solvent is methanol.

5. A method according to claim 1, wherein the surfactant is sodium tetradecyl sulfate.

6. A method according to claim 5, including the additional step of washing the fingerprints with a washing solution of $8 \times 10^{-4}$M of a non-fluorescent chelating agent in water.

7. A method according to claim 6, wherein the metal chelate is the tris chelate of thenoyltrifluoroacetone with two coordinating triocylphosphine oxide groups and the europium III ion.

8. A method according to claim 6, wherein the chelating agent is the sodium salt of ethylenediaminetetraacetic acid.

9. A method according to claim 1, wherein the group containing a polar functional group is R'$_3$ PO, in which R' is an alkyl group.

10. A method according to claim 9, wherein R' is butyl or octyl.

11. A method according to claim 1 wherein, the fingerprints are on porous or non-porous surfaces.

* * * * *